United States Patent [19]

LaMarre et al.

[11] Patent Number: 4,595,691

[45] Date of Patent: Jun. 17, 1986

[54] SYNERGISTIC BIOCIDE OF 2-(THIOCYANOMETHYLTHIO) BENZOTHIAZOLE WITH A MIXTURE OF 5-CHLORO-2-METHYL-4-ISOTHIAZOLIN-3-ONE AND 2-METHYL-4-ISOTHIAZOLIN-3-ONE

[75] Inventors: Thomas M. LaMarre, Aurora; Cynthia H. Martin, Joliet; Madelynn T. Wilharm, Woodridge, all of Ill.

[73] Assignee: Nalco Chemical Company, Oak Brook, Ill.

[21] Appl. No.: 757,695

[22] Filed: Jul. 22, 1985

[51] Int. Cl.[4] ............... A01N 43/78; C02F 9/00; D21H 5/22

[52] U.S. Cl. .................... 514/367; 210/631; 162/161

[58] Field of Search ............... 514/367, 372

[56] References Cited

U.S. PATENT DOCUMENTS

| | | | |
|---|---|---|---|
| 3,664,821 | 5/1972 | Shema et al. | 71/67 |
| 3,928,198 | 12/1975 | Brink et al. | 210/62 |
| 3,929,561 | 12/1975 | Shema et al. | 252/106 |
| 4,285,765 | 8/1981 | Pera et al. | 71/67 |
| 4,295,932 | 10/1981 | Pocius | 162/161 |
| 4,479,961 | 10/1984 | Martin | 514/367 |

OTHER PUBLICATIONS

Kull, Eisman, Sylwestrowicz, & Mayer, "Mixtures of Quaternary Ammonium Compounds and Long-Chain Fatty Acids as Antifungal Agents," *Applied Microbiology*, vol. 9, 1961, pp. 538–541.

*Primary Examiner*—Allen J. Robinson
*Attorney, Agent, or Firm*—John G. Premo; Donald G. Epple

[57] ABSTRACT

The combination of biocides,

A. 5-chloro-2-methyl-4-isothiazolin-3-one and 2-methyl-4-isothiazolin-3-one; and B. 2-(thiocyanomethylthio)-benzothiazole provide a synergistic material for controlling microorganisms in industrial process waters.

1 Claim, No Drawings

SYNERGISTIC BIOCIDE OF 2-(THIOCYANOMETHYLTHIO) BENZOTHIAZOLE WITH A MIXTURE OF 5-CHLORO-2-METHYL-4-ISOTHIAZOLIN-3-ONE AND 2-METHYL-4-ISOTHIAZOLIN-3-ONE

INTRODUCTION

The formation of slime by microorganisms is a problem which attends many systems. For example, lagoons, lakes, ponds, pools, and such systems as cooling water systems and pulp and paper mill systems, all possess conditions which are conductive to the growth and reproduction of slime-forming microorganisms. In both once-through and recirculating cooling systems, for example, which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms flourish on the tower proper while other organisms colonize and grow in such areas as the tower sump and the piping and passages of the cooling system. Such slime serves to deteriorate the tower structure in the case of wooden towers. In addition, the deposition of slime on metal surfaces promotes corrosion. Furthermore, slime carried through the cooling system plugs and fouls lines, valves, strainers, etc. and deposits on heat exchange surfaces. In the latter case, the impedance of heat transfer can greatly reduce the efficiency of the cooling system.

In pulp and paper mill systems, slime formed by microorganisms is also frequently and, in fact, commonly encountered. Fouling or plugging by slime also occurs in the case of pulp and paper mill systems. Of greater significance, the slime becomes entrained in the paper produced to cause breakouts on the paper machines with consequent work stoppages and the loss of production time or unsightly blemishes in the final product which result in rejects and wasted output. The previously discussed problems have resulted in the extensive utilization of biocides in cooling water and pulp and paper mill systems. Materials which have enjoyed widespread use in such applications include chlorine, organo-mercurials, chlorinated phenols, organo-bromines, and various organo-sulfur compounds. All of these compounds are generally useful for this purpose but each is attended by a variety of impediments. For example, chlorination is limited both by its specific toxicity for slime-forming organisms at economic levels and by the ability of chlorine to react which results in the expenditure of the chlorine before its full biocidal function may be achieved. Other biocides are attended by odor problems and hazards in respect to storage, use or handling which limit their utility. To date, no one compound or type of compound has achieved a clearly established predominance in respect to the applications discussed. Likewise, lagoons, ponds, lakes, and even pools, either used for pleasure purposes or used for industrial purposes for the disposal and storage of industrial wastes, become, during the warm weather, beseiged by slime due to microorganism growth and reproduction. In the case of the recreation areas, the problem of infection, etc. is obvious. In the case of industrial storage or disposal of industrial materials, the microorganisms cause additional problems which must be eliminated prior to the materials use or the waste is treated for disposal.

Naturally, economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides have exhibited a prolonged biocidal effect. Instead, their effectiveness is rapidly reduced as the result of exposure to physical conditions such as temperature, association with ingredients contained by the system toward which they exhibit an affinity or substantivity, etc., with a resultant restriction or elimination of their biocidal effectiveness.

As a consequence, the use of such biocides involves their continuous or frequent addition to systems to be treated and their addition to a plurality of points or zones in the systems to be treated. Accordingly, the cost of the biocide and the labor cost of such means of applying it are considerable. In other instances, the difficulty of access to the zone in which slime formation is experienced precludes the effective use of a biocide. For example, in a particular system there is no access to an area at which slime formation occurs and it may only be applied at a point which is upstream in the flow system. However, the physical or chemical conditions, e.g., chemical reactivity, thermal degradation, etc. which exist between the point at which the biocide may be added to the system and the point at which its biocidal effect is desired render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at a plurality of points, and even then a graduated biocidal effect will be experienced between one point of addition to the system and the next point downstream at which the biocides may be added. In addition to the increased cost of utilizing and maintaining plural feed points, gross ineconomies in respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

It is now known that the mixture of 75% 5-chloro-2-methyl-4-isothiazolin-3-one and 25% 2-methyl-4-isothiazolin-3-one which is sold under the tradename of Kathon-886 By Rohm and Haas may be blended with certain sulfones to produce a synergistic biocide. This is the subject matter of U.S. Pat. No. 3,929,561.

It is also known that Kathon-886 may be synergistically combined with either chlorine or chlorine dioxide to provide an improved microbiocide for treating aqueous systems of the type described above. This is described in U.S. Pat. No. 4,295,932.

Kathon-886 is effective at low dosages, e.g. a few parts per million, for treating industrial systems contaminated with a wide variety of microorganisms. These microorganisms include bacteria, molds, fungi, yeast and algae. In many cases, however, in order to achieve good control of microbiological growth in industrial cooling systems, Kathon-886 must be used at high dosages, e.g. in excess of 10 ppm. When such badly contaminated systems are treated with Kathon-886, it is relatively impossible to reduce the total count to a low level. Due to the high cost of Kathon-886, it is, therefore, not practical to use this material for controlling aqueous industrial systems which are heavily contaminated by microorganisms. Such systems containing heavy microorganism contamination are the type of system which benefit most from the practice of the instant invention.

These heavily contaminated systems are often further characterized as containing large amounts of deposits which are composed of dead microorganism masses. In severe cases they can often have the appearance of bearded slimes.

THE INVENTION

The invention comprises a synergistic biocidal composition useful in treating industrial process waters to prevent and control the growth of microorganisms, which composition comprises:

A. from 5–95% by weight of 75% 5-chloro-2-methyl-4-isothiazolin-3-one and 25% 2-methyl-4-isothiazolin-3-one; and B. from 95–5% by weight of 2-(thiocyanomethylthio)-benzothiazole.

This combination is effective at low dosages, e.g. 1–10 ppm.

Evaluation of the Invention

The synergism of these two components is demonstrated by adding 2-(thiocyanomethylthio)-benzothiazole (commercially known as TCMTB) and a mixture of 5-chloro-2-methyl-4-isothiazolin-3-one and 2-methyl-4-isothiazolin-3-one (commercially known as Kathon) in varying ratios over a range of concentrations to liquid nutrient medium. In this study of the control of bacterial growth, the nutrient medium was tryptone glucose extract agar. The concentrations of the above toxicants were added to aliquots of medium at a temperature of 50° C. Once treated, the medium was poured into sterile Petri dishes and allowed to solidify. Each test plate was inoculated with a bacterial suspension containing 0.1 ml of a nutrient broth culture of *Pseudomonas aeruginosa*. After an incubation at 37° C. for over forty-eight hours, the lowest concentration of each toxicant or of each ratio of the combined toxicants that prevented growth on the agar was taken as the end point.

The end points of each of the ratios tested were then compared with end points of the concentrations of the pure toxicants. Synergism was determined according to the industrially-accepted method described by S. C. Kull, P. C. Eisman, H. D. Sylwestrowicz, and R. L. Mayer in *Applied Microbiology*, Vol. 9, pages 538–541 (1936), which is herein included as reference.

As regards the Kull, et al. document, the data here presented can be described as follows:

$Q_A$ = the ppm of actives of TCMTB alone which produced an end point $Q_a$ = the ppm of actives of TCMTB, in combination, which produced an endpoint $Q_B$ = the ppm of actives of Kathon alone which produced an endpoint $Q_b$ = the ppm of actives of Kathon, in combination, which produced an endpoint if $\dfrac{Q_a}{Q_A} + \dfrac{Q_b}{Q_B}$ < 1 indicates synergy > 1 indicates antagonism
= 1 indicates additivity

TABLE I
SYNERGISM STUDY FOR COMBINATION BIOCIDES AGAINST BACTERIA

Growth: +
No Growth: −
Control Culture: 3.00 × 10$^7$ organisms per ml

| Ratio TCMTB/ KATHON | Concentrations (ppm) | | | | | | | | | | | |
|---|---|---|---|---|---|---|---|---|---|---|---|---|
| | 0.3 | 0.6 | 1.0 | 1.5 | 3.0 | 5.0 | 7.5 | 10 | 20 | 30 | 40 | 50 |
| 100/0 | + | + | + | + | + | + | + | + | − | − | − | − |
| 0/100 | + | + | + | + | − | − | − | − | − | − | − | − |
| 90/10 | + | + | + | + | + | + | + | − | − | − | − | − |
| 10/90 | + | + | + | − | − | − | − | − | − | − | − | − |
| 75/25 | + | + | + | + | + | − | − | − | − | − | − | − |
| 25/75 | + | + | + | − | − | − | − | − | − | − | − | − |
| 50/50 | + | + | + | + | − | − | − | − | − | − | − | − |

| Ratio TCMTB/KATHON | $\dfrac{Q_a}{Q_A} + \dfrac{Q_b}{Q_B}$ | Rating |
|---|---|---|
| 90/10 | 0.783 | <1 Synergy |
| 10/90 | 0.458 | <1 Synergy |
| 75/25 | 0.604 | <1 Synergy |
| 25/75 | 0.394 | <1 Synergy |
| 50/50 | 0.575 | <1 Synergy |

$Q_A$ = 20 ppm active TCMTB
$Q_B$ = 3 ppm active KATHON

A. 90/10
   $Q_a$ = 10 ppm × .90 = 9
   $Q_b$ = 10 ppm × .10 = 1

$$\dfrac{9}{20} + \dfrac{1}{3} = 0.783$$

B. 10/90
   $Q_a$ = 1.5 ppm × .10 = 0.15
   $Q_b$ = 1.5 ppm × .90 = 1.35

$$\dfrac{.15}{20} + \dfrac{1.35}{3} = 0.458$$

C. 75/25
   $Q_a$ = 5 ppm × 0.75 = 3.75
   $Q_b$ = 5 ppm × 0.25 = 1.25

$$\dfrac{3.75}{20} + \dfrac{1.25}{3} = 0.604$$

D. 25/75
   $Q_a$ = 1.5 ppm × 0.25 = .375
   $Q_b$ = 1.5 ppm × 0.75 = 1.125

$$\dfrac{.375}{20} + \dfrac{1.125}{3} = 0.394$$

E. 50/50
   $Q_a$ = 3 ppm × 0.50 = 1.5
   $Q_b$ = 3 ppm × 0.50 = 1.5

$$\dfrac{1.5}{20} + \dfrac{1.5}{3} = 0.575$$

We claim:

1. A synergistic biocidal composition useful in treating industrial process waters to prevent and control the growth of Pseudomonas bacteria, which composition comprises:

A. from 10–90% by weight of 75% 5-chloro-2-methyl-4-isothiazolin-3-one and 25% 2-methyl-4-isothiazolin-3-one; and B. from 90–10% by weight of 2-(thiocyanomethylthio)-benzothiazole.

* * * * *